United States Patent [19]

Bertin et al.

[11] Patent Number: 4,503,058
[45] Date of Patent: Mar. 5, 1985

[54] THERAPEUTICALLY USEFUL 3,7A-DIAZACYCLOHEPTA[j,k]FLUORENE DERIVATIVES

[75] Inventors: Jean Bertin, Clamart; Jonathan R. Frost, Cachan, both of France

[73] Assignee: Synthelabo, Paris, France

[21] Appl. No.: 446,368

[22] Filed: Dec. 2, 1982

[30] Foreign Application Priority Data

Dec. 3, 1981 [FR] France ................................ 81 22643

[51] Int. Cl.³ .................... C07D 471/16; A61K 31/55
[52] U.S. Cl. .................................. 514/214; 260/244.4
[58] Field of Search ..................... 260/244.4; 424/244, 424/256

[56] References Cited

U.S. PATENT DOCUMENTS 4,190,657  2/1980  Koletar et al. ............... 424/256 DR
4,228,168  10/1980  Sato et al. ........................... 424/256

FOREIGN PATENT DOCUMENTS 161389  5/1980  Japan .................................. 424/256

OTHER PUBLICATIONS

Belg. 882,024, Chem. Abstracts 94:103644h (1981).

Primary Examiner—Mark L. Berch
Assistant Examiner—William A. Teoli, Jr.
Attorney, Agent, or Firm—Wegner & Bretschneider

[57] ABSTRACT

Compounds of the formula:

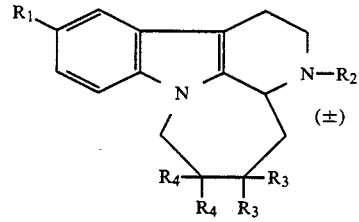

wherein $R_1$ represents hydrogen, chlorine or methoxy, $R_2$ represents hydrogen, methyl or benzyl, and $R_3$ and $R_4$ represent hydrogen, or $R_3$ represents methyl and $R_4$ represents hydrogen or $R_3$ represents hydrogen and $R_4$ represents methyl, are new compounds useful in therapy as they possess an antianoxic activity.

6 Claims, No Drawings

THERAPEUTICALLY USEFUL 3,7A-DIAZACYCLOHEPTA[j,k]FLUORENE DERIVATIVES

DESCRIPTION

The present invention relates to new therapeutically useful 3,7a-diazacyclohepta[j,k]fluorene derivatives, to their preparation and to pharmaceutical compositions containing them.

The compounds of the present invention correspond to the general formula:

wherein $R_1$ represents a hydrogen or chlorine atom or a methoxy radical, $R_2$ represents a hydrogen atom or the methyl or benzyl radical, and $R_3$ and $R_4$ represent hydrogen atoms, or $R_3$ represents the methyl radical and $R_4$ represents a hydrogen atom, or $R_3$ represents a hydrogen atom and $R_4$ represents the methyl radical, and pharmacologically-acceptable acid addition salts thereof.

The compounds of general formula (I) can exist in the form of racemates or enantiomers, and all such forms are part of the invention.

The preferred compounds of the invention are those of general formula (I) wherein the symbols $R_1$, $R_2$, $R_3$ and $R_4$ each represent a hydrogen atom.

According to the invention, the compounds of the invention are prepared according to the following reaction scheme:

Scheme wherein the various symbols are as hereinbefore defined.

The carbonyl radical of the starting compound (II) is reduced to methylene (i.e. $H_2C=$) with a mixture of lithium aluminium hydride and aluminium chloride to give a compound of general formula (I).

When it is desired to obtain a compound of general formula (I) wherein $R_2$ is hydrogen, it is also possible to debenzylate a corresponding compound of general formula (I) wherein $R_2$ is benzyl (i.e. $C_6H_5CH_2-$) by catalytic hydrogenation.

The starting compounds of general formula (II) wherein $R_1$, $R_3$ and $R_4$ are hydrogen atoms are described in published French Patent Application No. 2442236. The other starting compounds are described in the French patent application filed by SYNTHELABO on Dec. 3, 1981 and given the number 8122642 and also in our U.S. patent application filed on even date herewith.

Pharmacologically-acceptable acid addition salts of the compounds of general formula (I) can be obtained by methods known per se, for example by reacting the basic compound with an acid, the anion of which is relatively innocuous to the animal organism in therapeutic doses of the salts, e.g. hydrochloric, methanesulphonic, fumaric or maleic acid.

The following Examples illustrate the preparation of the compounds of the invention.

The analyses and the IR and NMR spectra confirmed the structure of the compounds.

EXAMPLE 1

3-Benzyl-1,2,3,3a,4,5,6,7-octahydro-3,7a-diazacyclohepta[j,k]fluorene 0.265 g of aluminium chloride is introduced into 10 ml of tetrahydrofuran, this being followed by the addition of 0.114 g of lithium aluminium hydride and then by the addition of 0.33 g of 3-benzyl-7-oxo-1,2,3,3a,4,5,6,7-octahydro-3,7a-diazacyclohepta[j,k]fluorene in small amounts. The mixture is stirred at ambient temperature for one hour. 1.5 ml of concentrated sodium hydroxide solution are added, followed by ethyl acetate. The mixture is filtered and the organic phase is decanted, washed with water, dried over Na$_2$SO$_4$ and then evaporated to dryness.

The product obtained is recrystallised from diisopropyl ether. Its melting point is 104°–105° C.

EXAMPLE 2

1,2,3,3a,4,5,6,7-Octahydro-3,7a-diazacyclohepta[j,k]fluorene and its hydrochloride In a Parr apparatus, 1.5 g of the compound obtained as described in Example 1, dissolved in 50 ml of methanol, are hydrogenated under a pressure of 0.35 MPa, at ambient temperature, in the presence of a 10% Pd/C catalyst and hydrochloric acid. After the catalyst has been filtered off, the reaction mixture is evaporated.

The hydrochloride formed is filtered off and recrystallised from methanol. Its melting point is 294°–296° C. (dec.)

EXAMPLE 3

10-Chloro-1,2,3,3a,4,5,6,7-octahydro-3,7a-diazacyclohepta[j,k]fluorene 0.586 g of aluminium chloride is added to 25 ml of tetrahydrofuran contained in a 100 ml three-necked round-bottomed flask, under a nitrogen atmosphere, and the mixture is stirred for 30 minutes until the solid has dissolved. 0.250 g of lithium aluminium hydride is then added, the stirring being continued for 30 minutes. 0.6 g of 10-chloro-7-oxo-1,2,3,3a,4,5,6,7-octahydro-3,7a-diazacyclohepta[j,k]fluorene is then introduced with a spatula and the mixture is stirred at ambient temperature for two hours and then left to stand overnight. 4 ml of concentrated sodium hydroxide solution are then introduced cautiously, followed by 30 ml of water, and the mixture is extracted with ethyl acetate. The organic phase is washed with water, dried over magnesium sulphate and then evaporated to dryness. The oil thus obtained is transferred to a silica column with a 90/10 mixture of chloroform and methanol as the eluant. The oil collected in this way crystallises from pentane. The crystals melt at 94°–6° C.

The following Table by reference to general formula (I) illustrates other compounds according to the invention obtained by analogous methods.

TABLE (I)

[Structure diagram with substituents $R_1$, $R_2$, $R_3$, $R_4$]

| Compound | $R_1$ | $R_2$ | $R_3$ | $R_4$ | Form | Melting point (°C.) |
|---|---|---|---|---|---|---|
| 1 | H | $C_6H_5CH_2$ | H | H | base | 104–5 |
|   |   |   |   |   | HCl | 218–20 |
| 2 | H | H | H | H | HCl | 294–6 (dec) |
| 3 | Cl | H | H | H | base | 94–6 |
| 4 | Cl | $C_6H_5CH_2$ | H | H | HCl | 256–8 |
| 5 | H | $CH_3$ | $CH_3$ | H | HCOOH<br>‖<br>HCOOH | 175 |
| 6 | H | $C_6H_5CH_2$ | $CH_3$ | H | HCl | 195 |
| 7 | H | $CH_3$ | H | $CH_3$ | HCOOH<br>‖<br>HCOOH | 198–9 |
| 8 | H | H | $CH_3$ | H | HCOOH<br>‖<br>HCOOH | 180–1 |
| 9 | H | $C_6H_5CH_2$ | H | $CH_3$ | HCOOH<br>‖<br>HCOOH | 196–8 |
| 10 | H | H | H | $CH_3$ | HCOOH<br>‖<br>HCOOH | 186–7 |
| 11 | $CH_3O$ | $C_6H_5CH_2$ | H | H | HCOOH<br>‖<br>HCOOH | 168–70 |
| 12 | $CH_3O$ | H | H | H | HCl | 294–6 |

The compounds of the invention were subjected to pharmacological tests for the purpose of demonstrating their value in therapy.

Acute toxicity to mice

The compounds are administered to the test animals in increasing doses. The toxicity of the compounds is expressed by the dose, in mg per kg of body weight, at which half of the animals in the batch corresponding to each test survive. It is thus found that, by intraperitoneal administration, the $LD_{50}$ values of the compounds range from 30 mg/kg to more than 1000 mg/kg whereas, by oral administration, they range from 100 mg/kg to more than 1000 mg/kg.

Antianoxic activity

When administered intraperitoneally, the compounds of the invention prolong the life of mice placed in an oxygen-depleted atmosphere (produced by creating a partial vacuum in a closed chamber in which the pressure is brought to $2.5 \times 10^4$ Pa (190 mm Hg) in 30 seconds using a vacuum pump).

The activity of the compounds is expressed by the $AD_{100}$, that is to say the dose in mg/kg animal body weight which prolongs the survival time of the treated animals by 100%, compared with the survival time of the control animals.

The $AD_{100}$ values of the compounds of the invention are between 2.9 and 8.3 mg/kg.

Total ischaemia test in mice

The survival time of the test animals is measured after they have been injected in the caudal vein with 0.1 ml of a saturated solution of magnesium chloride. The cardiac arrest which results causes cerebral ischaemia. The "survival time" is the period of time between the injection of the magnesium chloride and the last inspiratory movement of each mouse, which is considered as the final indication of function of the central nervous system.

The survival times of the animals treated with the compounds of the invention, administered intraperitoneally 10 minutes before the injection of the magnesium chloride, are compared with the survival times of the control animals, to which only the vehicle for the active substances has been administered.

The mice are studied in groups of 10 and the averages of the results of each group make it possible to plot a curve; this permits a graphical determination of the Effective Dose 3, $ED_3$, expressed in mg of active substance per kg of body weight, which prolongs the survival time by 3 seconds.

An increase of 3 seconds in the survival time is both statistically significant and reproducible.

The $ED_3$ values of the compounds of the invention range from 3 to 30 mg/kg.

The pharmacological study of the compounds of the invention shows that they possess an antianoxic activity and that they can be used in therapy for the treatment of vigilance disorders, in particular for combating the behavioural disorders attributable to cerebral vascular damage and to the cerebral sclerosis encountered in geriatrics, and also for the treatment of the absences due to cranial traumatisms, for the treatment of metabolic encephalopathies and for the treatment of depressive states.

The invention consequently includes all pharmaceutical compositions containing the compounds of the invention or their pharmacologically-acceptable acid addition salts as active principles, in association with any excipients which are suitable for their administration, in particular their oral or parenteral administration.

The daily dosage can range from 1 to 100 mg, administered parenterally, and from 5 to 500 mg, administered orally, the dose units containing, for example, 1 to 100 mg doses of active substance.

We claim:
1. A compound of the formula:

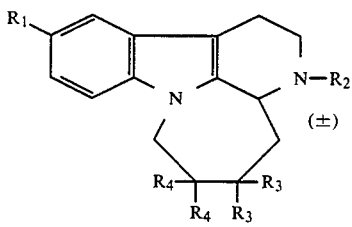

wherein $R_1$ represents a hydrogen or chlorine atom or a methoxy radical, $R_2$ represents a hydrogen atom or the methyl or benzyl radical, and $R_3$ and $R_4$ represents hydrogen atoms, or $R_3$ represents the methyl radical and $R_4$ represents a hydrogen atom or $R_3$ represents a hydrogen atom and $R_4$ represents the methyl radical, and its pharmacologically-acceptable acid addition salts.

2. A compound according to claim 1 which is 3-benzyl-1,2,3,3a,4,5,6,7-octahydro-3,7a-diazacyclohepta[j,k]fluorene and its pharmacologically-acceptable acid addition salts.

3. A compound according to claim 1 which is 1,2,3,3a,4,5,6,7-octahydro-3,7a-diazacyclohepta[j,k]fluorene and its pharmacologically-acceptable acid addition salts.

4. A compound according to claim 1 which is 10-chloro-1,2,3,3a,4,5,6,7-octahydro-3,7a-diazacyclohepta[j,k]fluorene and its pharmacologically-acceptable acid addition salts.

5. An antianoxic composition containing an effective amount of a compound as claimed in claim 1, or a pharmacologically-acceptable acid addition salt thereof, in association with a pharmaceutically-acceptable excipient.

6. A method for the treatment of a patient requiring antianoxic therapy, which comprises administering to a patient requiring such therapy an amount of a compound of the formula specified in claim 1, or a pharmacologically-acceptable acid addition salt thereof, effective to ameliorate the condition of the patient.

* * * * *